(12) United States Patent
Ebel et al.

(10) Patent No.: US 8,410,293 B2
(45) Date of Patent: Apr. 2, 2013

(54) PROCESS FOR THE PREPARATION OF CYCLIC ENOL ETHERS

(75) Inventors: Klaus Ebel, Lampertheim (DE); Bernhard Brunner, Heidelberg (DE); Christoph Stock, Ellerstadt (DE); Ralf Pelzer, Fürstenberg (DE)

(73) Assignee: BASF SE (DE)

( * ) Notice: Subject to any disclaimer, the term of this patent is extended or adjusted under 35 U.S.C. 154(b) by 0 days.

(21) Appl. No.: 13/536,036

(22) Filed: Jun. 28, 2012

(65) Prior Publication Data

US 2013/0005994 A1 Jan. 3, 2013

Related U.S. Application Data

(60) Provisional application No. 61/502,879, filed on Jun. 30, 2011.

(51) Int. Cl.
*C07D 309/18* (2006.01)
*C07D 311/74* (2006.01)
*C07D 307/28* (2006.01)
*C07D 307/79* (2006.01)

(52) U.S. Cl. ......... 549/396; 549/356; 549/462; 549/507

(58) Field of Classification Search .................. 549/356, 549/396, 462, 507
See application file for complete search history.

(56) References Cited

U.S. PATENT DOCUMENTS

| 3,856,815 | A | 12/1974 | Hopp et al. |
| 3,890,353 | A | 6/1975 | Becker |
| 4,056,541 | A | 11/1977 | Hoffman et al. |
| 4,268,445 | A | 5/1981 | Kropp et al. |
| 6,008,185 | A | 12/1999 | Bertram et al. |

FOREIGN PATENT DOCUMENTS

| DE | 2136496 A1 | 2/1973 |
| DE | 2511410 A1 | 9/1976 |
| DE | 2906296 A1 | 8/1980 |
| EP | 0862911 A2 | 9/1998 |
| GB | 1266092 A | 3/1972 |
| JP | 2010095447 A | 4/2010 |
| WO | WO-2008066299 A1 | 6/2008 |
| WO | WO-2008133441 A1 | 11/2008 |

OTHER PUBLICATIONS

U.S. Appl. No. 61/502,883, filed Jun. 30, 2011, Brunner et al.
Danet, Michele, et al., "Enantioselective Synthesis of the Originally Proposed Usneoidone Structure: Evidence for a Structural Revision", Eur. J. Org. Chem., (2004), pp. 1911-1922.
Bonifazi, Evelyn L., et al., "Antiproliferative Activity of Synthetic Naphthoquinones Related to Lapachol. First Synthesis of 5-Hyrdoxylapachol", Bioorganic & Medicinal Chemistry, vol. 18, (2010), pp. 2621-2630.
Thomas, Alan F., et al., "Homologues of ρ-Menthane Derivatives in Roman Camomile" Helvetica Chimica Acta, vol. 64, Fasc. 5, No. 136, (1981), pp. 1488-1495.
Zakharkin, L.I., et al., "Syntheses of 2-Oxabicyclo[4.10.0]Hexadec-1(6)-Ene from Cyclododecanone", Russian Chemical Bulletin, vol. 43, No. 4, (1994), pp. 608-611.

*Primary Examiner* — Bernard Dentz
(74) *Attorney, Agent, or Firm* — Novak Druce Connolly Bove + Quigg LLP

(57) ABSTRACT

The present invention relates to a process for the preparation of cyclic enol ethers.

7 Claims, No Drawings

PROCESS FOR THE PREPARATION OF CYCLIC ENOL ETHERS

CROSS-REFERENCE TO RELATED APPLICATIONS

This application claims benefit (under 35 USC 119(e)) of U.S. Provisional Application 61/502,879, filed Jun. 30, 2011, which is incorporated by reference.

The present invention relates to a process for the preparation of cyclic enol ethers.

Cyclic enol ethers are important intermediates in the synthesis of macrocyclic lactones, which are used as fragrances. For example, U.S. Pat. No. 3,890,353 describes the preparation of saturated 15-pentadecanolide (Exaltolide®) of the formula (a),

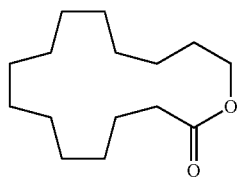

(a)

where the cyclic enol ether 13-oxa-1,12-didehydrobicyclo[10.4.0]hexadecane of the formula (b) serves as starting material.

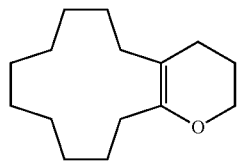

(b)

In addition to the 16-ring lactones described above, 15-ring lactones are also described as musk-like fragrances. For example, EP 0 862 911 describes saturated and unsaturated 15-ring lactones of the formulae (d1) and (d2), where R is methyl or hydrogen.

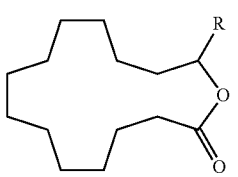

(d1)

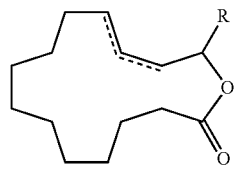

(d2)

The 15-ring lactones can be prepared starting from the corresponding cyclic enol ether of the formula (e).

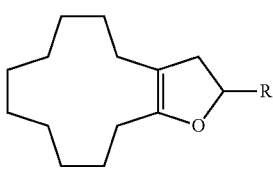

(e)

where R is H or Me

The preparation of cyclic enol ethers, which are suitable as fragrances or for producing fragrances, is described, for example, in GB 1266092, DE 2136496, U.S. Pat. No. 3,890,353, DE 25 11 410, DE 29 06 296 or JP 2010-95447.

In some cases, the starting materials for the preparation of the cyclic enol ethers are not easily accessible and/or the preparation of the cyclic enol ethers proceeds via multistage syntheses with at times poor yields, sometimes the reaction conditions for the cyclization are very drastic, for example by virtue of using relatively large amounts of concentrated sulfuric acid, or the processing of the cyclic enol ethers is still not satisfactory from the point of view of cost, or large excesses of reagents or starting materials are required.

Proceeding from this prior art, the object was to find flexible and more efficient synthesis routes to fragrances of this type.

This object is achieved by a process for the preparation of cyclic enol ethers of the formulae (I) and/or (II)

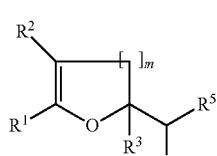

(I)

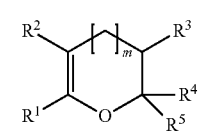

(II)

by cyclization of a starting compound of the formula (III)

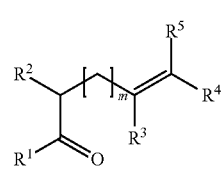

(III)

in which m is zero (0), one (1) or two (2), $R^1$ is an organic radical with 1 to 20 carbon atoms, $R^2$ is hydrogen or an organic radical having 1 to 20 carbon atoms, or the radicals $R^1$ and $R^2$, together with the atoms connecting them, form a mono- or polycyclic, substituted or unsubstituted ring system with 3 to 20 carbon atoms which can also comprise heteroatoms selected from the group consisting of the elements Si, N, P, O, and S, $R^3$ is hydrogen or an organic radical with 1 to 20 carbon atoms, $R^4$ is hydrogen or an organic radical with 1 to 20 carbon atoms, and $R^5$ is hydrogen or an organic radical with 1 to 20 carbon atoms.

in the presence of a Brønsted acid or Lewis acid, where the reaction is carried out as reactive distillation, where the formed cyclic enol ethers of the formulae (I) and/or (II) are separated off from the starting compound of the formula (III) by distillation from the reaction mixture.

The Brønsted acids which can be used in the process according to the invention are either organic or inorganic acids. Preference is given to Brønsted acids which themselves cannot react with the starting compound of the formula (III), i.e. are not consumed in a reaction, but merely serve as a proton source for a chemical reaction catalyzed by protons. Nonlimiting examples of particularly suitable Brønsted acids are sulfuric acid, phosphoric acid, methanesulfonic acid, p-toluenesulfonic acid, strong acidic ion exchangers, tetrafluoroboric acid, trifluoroacetic acid, formic acid or oxalic acid.

Lewis acids which can be used in the process according to the invention are, for example, aluminum trichloride, tin tetrachloride, titanium tetrachloride, zirconium tetrachloride, iron trichloride or nickel dichloride.

The amount of Brønsted acid or Lewis acid which is used in the process according to the invention can be varied within a wide range. In principle, the molar ratio of the Brønsted acid or Lewis acid to the compound of the formula (III) can be greater than, equal to or less than 1. In principle, traces of acid suffice to catalyze the cyclization.

Preferably, in the process according to the invention, the molar ratio of the Brønsted acid or Lewis acid, in particular of the Brønsted acid, to the compound of the formula (III) is not greater than 1, particularly preferably not greater than 0.15, very particularly preferably between 0.1 and 0.0005, in particular between 0.07 and 0.001.

Preferably, in the process according to the invention, the cyclization is carried out in the presence of a Brønsted acid. Preference is given here to using Brønsted acids with a pKa value of less than 5, particularly preferably less than 2.5, in particular less than 0. Very particularly preferably, the pKa value of the Brønsted acid is between −1.5 and −11.

A reactive distillation is a chemical process known in principle to the person skilled in the art in which a single-stage or multi-stage distillation is connected with a chemical reaction, in the present case a cyclization. The reaction product, in the present case a cyclic enol ether of the formulae (I) and/or (II), is separated off continuously by distillation from the starting material, a ketone.

Preferably, the reactive distillation and/or the cyclization reaction is carried out in a temperature range between 50° C. and 300° C., particularly preferably between 80° C. and 200° C.

Depending on the boiling points of the compounds to be separated, the person skilled in the art can usually ascertain, directly or after a few experiments, suitable measures with regard to the distillation columns which can be used, the required separation efficiency of such a column, and also the distillation parameters such as, for example, pressure, temperature and reflux ratio, and/or make a suitable selection in order to be able to carry out the process according to the invention in the desired manner.

Unless limited further, the substituents according to the present invention are defined as follows:

The term "organic radical with 1 to 20 carbon atoms", as used previously, refers, for example, to $C_1$-$C_{20}$-alkyl radicals, saturated $C_3$-$C_{20}$-heterocyclic radicals, $C_6$-$C_{20}$-aryl radicals, $C_2$-$C_{20}$-hetero-aromatic radicals or $C_7$-$C_{20}$-arylalkyl radicals, where the carbon-containing radical can comprise further heteroatoms selected from the group of the elements consisting of F, Cl, Br, I, N, P, Si, O and S and/or can be substituted with functional groups.

The term "alkyl", as used in the present case, includes linear and mono- and optionally also poly-branched saturated hydrocarbons, which may also be cyclic. Preference is given to a $C_1$-$C_{10}$-alkyl, such as methyl, ethyl, n-propyl, n-butyl, n-pentyl, n-hexyl, n-heptyl, n-octyl, n-nonyl, n-decyl, cyclopentyl, cyclohexyl, isopropyl, isobutyl, isopentyl, isohexyl, sec-butyl or tert-butyl.

The term "saturated heterocyclic radical", as used previously, refers, for example, to mono- or polycyclic, substituted or unsubstituted hydrocarbon radicals in which one or more hydro-carbons, CH groups and/or $CH_2$ groups are replaced by heteroatoms, preferably selected from the group consisting of the elements O, S, N and P. Preferred examples of substituted or unsubstituted saturated heterocyclic radicals are pyrrolidinyl, imidazolidinyl, pyrazolidinyl, piperidyl, piperazinyl, morpholinyl, tetrahydrofuranyl, tetrahydropyranyl, tetrahydrothiophenyl and the like, and also derivatives thereof substituted with methyl, ethyl, propyl, isopropyl and tert-butyl radicals.

The term "aryl", as used previously, refers, for example, to aromatic and optionally also condensed polyaromatic hydrocarbon radicals which may optionally be mono- or polysubstituted with linear or branched $C_1$-$C_{10}$-alkyl, $C_1$-$C_{10}$-alkoxy, $C_2$-$C_{10}$-alkenyl or halogen, in particular fluorine. Preferred examples of substituted or unsubstituted aryl radicals are in particular phenyl, fluorophenyl, 4-methylphenyl, 4-ethylphenyl, 4-n-propylphenyl, 4-isopropyl-phenyl, 4-tert-butylphenyl, 4-methoxyphenyl, 1-naphthyl, 9-anthryl, 9-phenanthryl, 3,5-dimethyl-phenyl, 3,5-di-tert-butylphenyl or 4-trifluoromethylphenyl.

The term "heteroaromatic radical", as used previously, refers, for example, to aromatic hydrocarbons in which one or more carbon atoms are replaced by nitrogen atoms, phosphorus atoms, oxygen atoms or sulfur atoms or combinations thereof. Like the aryl radicals, these can be optionally mono- or polysubstituted with linear or branched $C_1$-$C_{10}$-alkyl, $C_1$-$C_{10}$-alkoxy, $C_2$-$C_{10}$-alkenyl or halogen, in particular fluorine. Preferred examples are furyl, thienyl, pyrrolyl, pyridyl, pyrazolyl, imidazolyl, oxazolyl, thiazolyl, pyrimidinyl, pyrazinyl and the like, and also derivatives thereof substituted with methyl, ethyl, propyl, isopropyl and tert-butyl radicals.

The term "arylalkyl", as used previously, refers, for example, to aryl-containing substituents whose aryl radical is linked via an alkyl chain to the corresponding radical of the molecule. Examples are benzyl, substituted benzyl, phenethyl, substituted phenethyl and the like.

The radical $R^1$ is an organic radical with 1 to 20 carbon atoms, such as, for example, $C_1$-$C_{20}$-alkyl, $C_6$-$C_{20}$-aryl, arylalkyl or alkylaryl with 1 to 10, preferably 1 to 4, carbon atoms in the alkyl radical and 6 to 14, preferably 6 to 10, in particular 6, carbon atoms in the aryl radical, a saturated heterocyclic radical with 3 to 20 carbon atoms or a heteroaromatic radical with 3 to 20 carbon atoms having in each case at least one heteroatom selected from the group consisting of the elements N, P, O and S, in particular N, O and S, where the heteroaromatic radical can be substituted with further radicals $R^{10}$, where $R^{10}$ is an organic radical with 1 to 10, in particular 1 to 6, carbon atoms, such as, for example, $C_1$-$C_4$-alkyl, $C_6$-$C_{10}$-aryl, arylalkyl or alkylaryl with 1 to 4 carbon atoms in the alkyl radical and 6 to 10, preferably 6, carbon atoms in the aryl radical, and two or more radicals $R^{10}$ may be identical or different.

Preferably, $R^1$ is a linear $C_1$-$C_{10}$-, in particular $C_1$-$C_4$-alkyl radical, a branched $C_3$-$C_{10}$-, in particular $C_3$-$C_4$-alkyl radical, a $C_4$-$C_{10}$-, in particular $C_5$-$C_8$-cycloalkyl radical. Particularly preferably, $R^1$ is a linear $C_1$-$C_{10}$-, in particular $C_1$-$C_4$-alkyl radical.

The radical $R^2$ is hydrogen or an organic radical with 1 to 20 carbon atoms, such as, for example, $C_1$-$C_{20}$-alkyl, $C_6$-$C_{20}$-aryl, arylalkyl or alkylaryl with 1 to 10, preferably 1 to 4, carbon atoms in the alkyl radical and 6 to 14, preferably 6 to 10, in particular 6, carbon atoms in the aryl radical, a saturated heterocyclic radical with 3 to 20 carbon atoms or a heteroaromatic radical with 3 to 20 carbon atoms having in each case at least one heteroatom selected from the group consisting of the elements N, P, O and S, in particular N, O and S, where the heteroaromatic radical can be substituted with further radicals $R^{10}$.

Preferably, $R^2$ is a linear $C_1$-$C_{10}$-, in particular $C_1$-$C_4$-alkyl radical, a branched $C_3$-$C_{10}$-, in particular $C_3$-$C_4$-alkyl radical, a $C_4$-$C_{10}$-, in particular $C_5$-$C_8$-cycloalkyl radical. Particularly preferably, $R^2$ is a linear $C_1$-$C_{10}$-, in particular $C_1$-$C_4$-alkyl radical.

Alternatively, the radicals $R^1$ and $R^2$, together with the atoms connecting them, form a mono- or polycyclic, substituted or unsubstituted ring system with 3 to 20, preferably 5 to 14, carbon atoms, which can also comprise heteroatoms selected from the group consisting of the elements Si, N, P, O, and S. Preferably, the radicals $R^1$ and $R^2$ are together a divalent group —$(CH_2)_x$—, where x is an integer from 3 to 12, preferably 4 to 12, in particular 10.

The radical $R^3$ is hydrogen or an organic radical having 1 to 20 carbon atoms, such as, for example, $C_1$-$C_{20}$-alkyl, $C_6$-$C_{20}$-aryl, arylalkyl or alkylaryl with 1 to 10, preferably 1 to 4, carbon atoms in the alkyl radical and 6 to 14, preferably 6 to 10, in particular 6, carbon atoms in the aryl radical, a saturated heterocyclic radical with 3 to 20 carbon atoms or a heteroaromatic radical with 3 to 20 carbon atoms having in each case at least one heteroatom selected from the group consisting of the elements N, P, O and S, in particular N, O and S, where the heteroaromatic radical can be substituted with further radicals $R^{10}$.

Preferably, $R^3$ is hydrogen, a linear $C_1$-$C_{10}$-, in particular $C_1$-$C_4$-alkyl radical, a branched $C_3$-$C_{10}$-, in particular $C_3$-$C_4$-alkyl radical, a $C_4$-$C_{10}$-, in particular $C_5$-$C_8$-cycloalkyl radical. Particularly preferably, $R^3$ is hydrogen or methyl.

The radical $R^4$ is hydrogen or an organic radical with 1 to 20 carbon atoms, such as, for example, $C_1$-$C_{20}$-alkyl, $C_6$-$C_{20}$-aryl, arylalkyl or alkylaryl with 1 to 10, preferably 1 to 4, carbon atoms in the alkyl radical and 6 to 14, preferably 6 to 10, in particular 6, carbon atoms in the aryl radical, a saturated heterocyclic radical with 3 to 20 carbon atoms or a heteroaromatic radical with 3 to 20 carbon atoms having in each case at least one heteroatom selected from the group consisting of the elements N, P, O and S, in particular N, O and S, where the heteroaromatic radical can be substituted with further radicals $R^{10}$.

Preferably, $R^4$ is hydrogen, a linear $C_1$-$C_{10}$-, in particular $C_1$-$C_4$-alkyl radical, a branched $C_3$-$C_{10}$-, in particular $C_3$-$C_4$-alkyl radical, a $C_4$-$C_{10}$-, in particular $C_5$-$C_8$-cycloalkyl radical. $R^4$ is particularly preferably hydrogen or methyl.

The radical $R^5$ is hydrogen or an organic radical with 1 to 20 carbon atoms, such as, for example, $C_1$-$C_{20}$-alkyl, $C_6$-$C_{20}$-aryl, arylalkyl or alkylaryl with 1 to 10, preferably 1 to 4, carbon atoms in the alkyl radical and 6 to 14, preferably 6 to 10, in particular 6, carbon atoms in the aryl radical, a saturated heterocyclic radical with 3 to 20 carbon atoms or a heteroaromatic radical with 3 to 20 carbon atoms having in each case at least one heteroatom selected from the group consisting of the elements N, P, O and S, in particular N, O and S, where the heteroaromatic radical can be substituted with further radicals $R^{10}$.

Preferably, $R^5$ is hydrogen, a linear $C_1$-$C_{10}$-, in particular $C_1$-$C_4$-alkyl radical, a branched $C_3$-$C_{10}$-, in particular $C_3$-$C_4$-alkyl radical, a $C_4$-$C_{10}$-, in particular $C_5$-$C_8$-cycloalkyl radical. $R^5$ is particularly preferably hydrogen or methyl.

The indice m is zero (0), one (1) or two (2). In the case of compounds of the formula (I), m is preferably one (1) or two (2) and, in the case of compounds of the formula (II), m is preferably zero (0) or one (1). Very particularly preferably, m is one (1) or two (2), in particular one (1).

The formation either of the cyclic enol ether of the formula (I) and/or of the formula (II) starting from a specific starting compound of the formula (III) depends decisively on which carbon atom of the double bond in the starting compound, either the radical $R^3$ or the carbon atom carrying the radicals $R^4$ and $R^5$, the more stable carbocation is formally able to form through protonation of the double bond. For example, in cases where m is 1, $R^3$ is methyl and $R^4$ and $R^5$ are hydrogen, cyclic enol ethers of the formula (I) are formed, and in cases where m is 1, $R^3$ is hydrogen and $R^4$ and $R^5$ are methyl, cyclic enol ethers of the formula (II) are formed.

Preferably, in the process according to the invention, the indices in the formula (I), (II) and (III) are defined as follows.

The radical $R^1$ is a $C_1$-$C_{10}$-, preferably $C_1$-$C_4$-alkyl radical, preferably a linear $C_1$-$C_{10}$-, preferably $C_1$-$C_4$-alkyl radical.

The radical $R^2$ is a $C_1$-$C_{10}$-, preferably $C_1$-$C_4$-alkyl radical, preferably a linear $C_1$-$C_{10}$-, preferably $C_1$-$C_4$-alkyl radical.

Alternatively, the radicals $R^1$ and $R^2$ are together a divalent group —$(CH_2)_x$—, where x is an integer from 3 to 12, preferably 4 to 12, in particular 10.

The radical $R^3$ is hydrogen or methyl.
The radical $R^4$ is hydrogen or methyl.
The radical $R^5$ is hydrogen or methyl.

The indice m is zero (0), one (1) or two (2). In the case of compounds of the formula (I), m is preferably one (1) or two (2) and in the case of compounds of the formula (II), m is preferably zero (0) or one (1). Very particularly preferably, m is one (1) or two (2), in particular one (1).

Preference is likewise given to a process according to the invention as described previously, where the starting compound of the formula (III), which is a compound of the formula (IIIa) or a compound of the formula (IIIb),

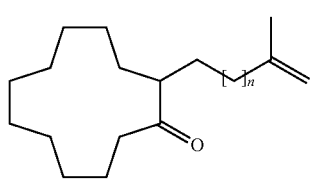

(IIIa)

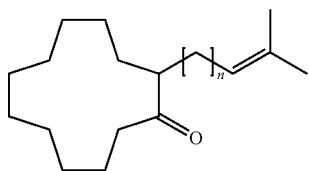

is reacted to give the corresponding cyclic enol ether of the formula (IIa),

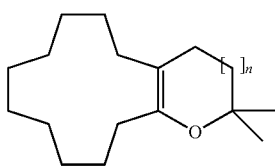

in which, in the formulae (IIa), (IIIa) and (IIIb)
n is zero (0) or one (1).

Particularly preferably, in compounds of the formula (IIIa), n is zero (0), which leads to the formation of the 5-membered cycloenol ether, and in compounds of the formulae (IIIb), n is 1, which leads to the formation of the 6-membered cycloenol ether.

The invention is illustrated by the following examples, although these do not limit the invention.

EXAMPLE 1

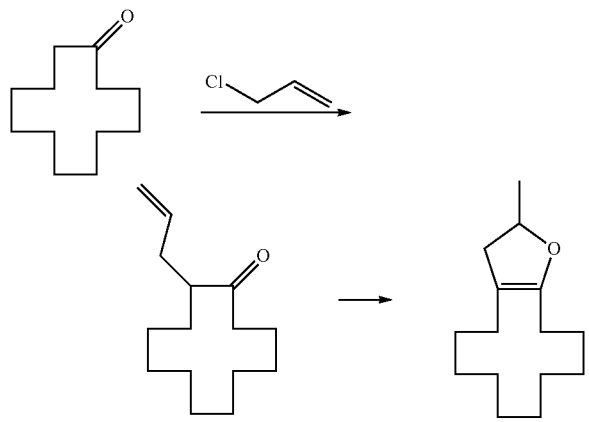

Allylation:

CDon (364.6 g), toluene (360 ml), tetrabutylammonium iodide (7.6 g) and sodium hydroxide solution (50% strength, 480 g) were introduced into the reactor and heated to 90° C. with stirring (400 rpm). At an internal temperature of 90° C., the metered addition of allyl chloride (306.1 g) was started, during which the temperature in the reactor dropped and reflux started. Total metering time: 3 h. The two-phase reaction mixture was then stirred overnight at 94° C. The reaction solution was then cooled to RT. At 65° C., 500 ml of water were added in order to dissolve the accumulated solid in the aqueous phase. Following phase separation, the organic phase was washed twice with 500 ml of water. The organic phase was then also washed with 500 g of 10% strength sulfuric acid. The aqueous phases were discarded in each case.

Cyclization:

213.5 g of allylation product are admixed with 5 ml of sulfuric acid in a distillation flask. In the distillation apparatus with 30 cm packed column (3 mm metal Raschig rings) and Normag column head, a vacuum of 2 mbar was applied, and 163.2 g of product were distilled off at a bottom temperature of 138-142° C. (overhead temperature 108-115° C.).

EXAMPLE 2

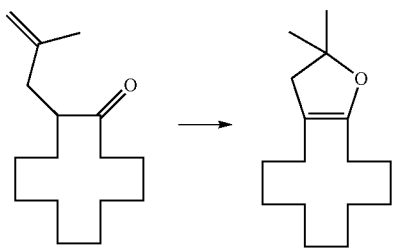 [SMILES: C=C(C)CC1CCCCCCCCCCC1=O ; CC1(C)CC2=C(CCCCCCCCCC2)O1]

Methallylcyclododecanone was prepared starting from CDon and methallyl chloride, analogously as described in example 1 in the allylation section.

Brønsted Acid Catalysis

In a 1000 ml three-neck flask with 30 cm Sulzer column and Normag column head, 1006 g of methallylcyclododecanone were introduced as initial charge and admixed with 20 g of concentrated sulfuric acid. A vacuum of 1 mbar was applied, the oil-bath temperature was increased to 140° C. At a bottom temperature of 128-135° C., the bicycle was slowly distilled out of the reaction mixture (overhead temperature 91-96° C.). In total, 866.35 g of product could be distilled out of the reaction mixture.

Lewis Acid Catalysis

In a 500 ml distillation flask with 30 cm packed column (3 mm wire rings) and Normag column head, 200 g of 2-(2-methallyl)cyclododecanone were introduced as initial charge and admixed with 2 g of aluminum chloride. A vacuum of 2 mbar was applied, the oil-bath temperature was slowly increased to 175° C. At a bottom temperature of 153-156° C., the product was distilled out of the reaction mixture (overhead temperature 121-123° C.). In total, 140.5 g of product could be distilled out of the reaction mixture.

EXAMPLE 3

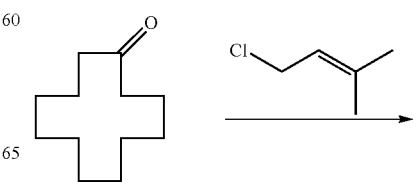

-continued

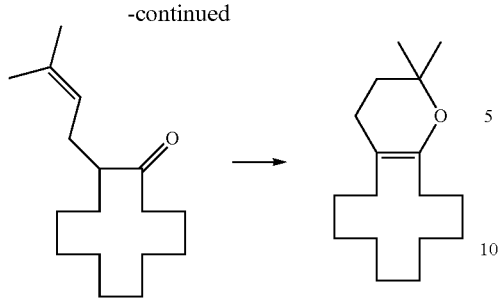

CDon (364.6 g), toluene (360 ml), tetrabutylammonium iodide (7.6 g) and sodium hydroxide solution (50% strength, 480 g) were introduced into the reactor and heated to 90° C. with stirring (400 rpm). At an internal temperature of 90° C., the metered addition of 1-chloro-3-methyl-2-butene (313.7 g) was started. The temperature was held at 90° C. during the entire addition. Total metering time: 3 h. The two-phase reaction mixture was after-stirred at 90° C. for 5 h. The reaction solution was then cooled to RT. At 65° C., 500 ml of water were added in order to dissolve the accumulated solid in the aqueous phase. Following phase separation, the organic phase was washed twice with 500 ml of water. The organic phase was then also washed with 500 g of 10% strength sulfuric acid. The aqueous phases were discarded in each case.

7 g of conc. sulfuric acid were added to 278 g of the intermediate product and then the solution was transferred to a 1 l distillation flask and distilled in a 70 cm packed column (3 mm metal Raschig rings) with reflux divided at a bottom temperature of 185° C., an overhead temperature of 130-135° C., a pressure of 3 mbar and a reflux ratio of 40:1 to 60:1. 191.7 g of the product could be distilled out of the reaction mixture.

EXAMPLE 4

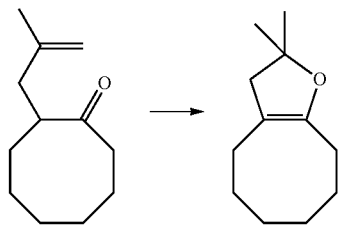

2-Methallylcyclooctanone was prepared starting from cyclooctanone and methallyl chloride, analogously as described in example 1 in the allylation section.

302.8 g of 2-methallylcyclooctanone were introduced as initial charge in a 1 l distillation flask with 30 cm packed column (3 mm wire rings), Normag column head and vacuum regulator. 3 g of concentrated sulfuric acid were added and a vacuum of 5 mbar was applied. The oil-bath temperature was increased slowly to 130° C. At a bottom temperature of 100-105° C., the bicycle formed was slowly distilled out of the reaction mixture. (Overhead temperature 77° C.). In total, 228.2 g of bicycle with a purity of >96% could be obtained as fractions.

EXAMPLE 5

3-Methallyl-4-heptanone was prepared starting from 4-heptanone and methallyl chloride, analogously as described in example 1 in the allylation section.

268 g of 3-methallyl-4-heptanone were introduced as initial charge in a 1 l distillation flask with 30 cm packed column (3 mm wire rings), Normag column head and vacuum regulator, and admixed with 2.68 g of concentrated sulfuric acid. A vacuum of 20 mbar was applied and the oil-bath temperature was increased to 110° C. At a bottom temperature of 83-88° C., the dihydro-furan formed was distilled out of the reaction mixture (overhead temperature 67-69° C.). In total, 208.1 g of product could be obtained.

The invention claimed is:

1. A process for the preparation of cyclic enol ethers of the formulae (I) and/or (II)

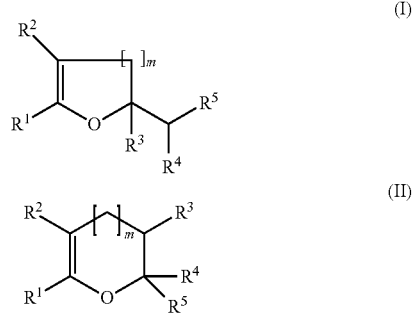

which comprises cyclization of a starting compound of the formula (III)

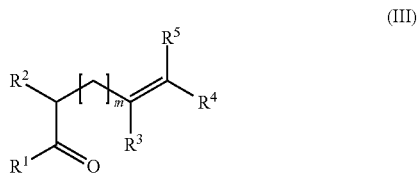

in which m is zero (0), one (1) or two (2), $R^1$ is an organic radical with 1 to 20 carbon atoms, $R^2$ is hydrogen or an organic radical having 1 to 20 carbon atoms, or the radicals $R^1$ and $R^2$, together with the atoms connecting them, form a mono- or polycyclic, substituted or unsubstituted ring system with 3 to 20 carbon atoms which can also comprise heteroatoms selected from the group consisting of the elements Si, N, P, O, and S, $R^3$ is hydrogen or an organic radical with 1 to 20 carbon atoms, $R^4$ is hydrogen or an organic radical with 1 to 20 carbon atoms, and $R^5$ is hydrogen or an organic radical with 1 to 20 carbon atoms, in the presence of a Brönstedt acid or Lewis acid, where the reaction is carried out as reactive distillation, where the formed cyclic enol ethers of the formulae (I) and/or (II) are separated off from the starting compound of the formula (III) by distillation from the reaction mixture.

2. The process according to claim 1, where the molar ratio of the Brönstedt acid or Lewis acid to the compound of the formula (III) is not greater than 1.

3. The process according to claim 1, where the cyclization is carried out in the presence of a Brönstedt acid with a pKa value of less than 5.

4. The process according to claim 1, in which, in the formulae (I), (II) and (III)

m is zero (0), one (1) or two (2),
$R^1$ is a $C_1$-$C_{10}$-alkyl radical,
$R^2$ is a $C_1$-$C_{10}$-alkyl radical,
or the radicals $R^1$ and $R^2$ together are a divalent group —$(CH_2)_x$—, where x is an integer from 3 to 12,
$R^3$ is hydrogen or methyl,
$R^4$ is hydrogen or methyl, and
$R^5$ is hydrogen or methyl.

5. The process according to claim 3, in which, in the formulae (I), (II) and (III)

$R^1$ is a $C_1$-$C_{10}$-alkyl radical,
$R^2$ is a $C_1$-$C_{10}$-alkyl radical,
or the radicals $R^1$ and $R^2$ together are a divalent group —$(CH_2)_x$—, where x is an integer from 3 to 12,
$R^3$ is hydrogen or methyl,
$R^4$ is hydrogen or methyl, and
$R^5$ is hydrogen or methyl.

6. The process according to claim 1, where the starting compound of the formula (III), which is a compound of the formula (IIIa) or a compound of the formula (IIIb),

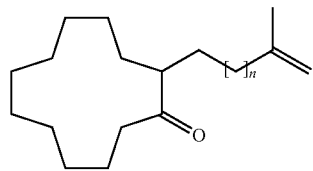
(IIIa)

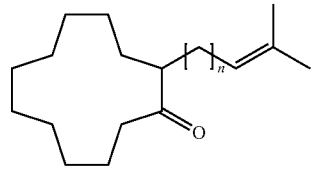
(IIIb)

is reacted to give the corresponding cyclic enol ether of the formula (IIa),

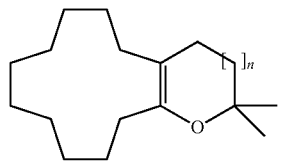
(IIa)

in which, in the formulae (IIa), (IIIa) and (IIIb)
n is zero (0) or one (1).

7. The process according to claim 5, where the starting compound of the formula (III), which is a compound of the formula (IIIa) or a compound of the formula (IIIb),

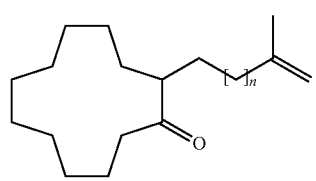
(IIIa)

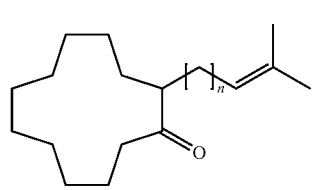
(IIIb)

is reacted to give the corresponding cyclic enol ether of the formula (IIa),

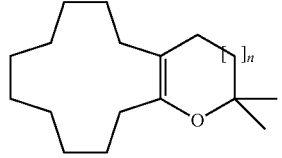
(IIa)

in which, in the formulae (IIa), (IIIa) and (IIIb)
n is zero (0) or one (1).

* * * * *